United States Patent
Fogarty et al.

(10) Patent No.: US 6,443,159 B1
(45) Date of Patent: Sep. 3, 2002

(54) ENDOSCOPIC LINTON PROCEDURE USING BALLOON DISSECTORS AND RETRACTORS

(75) Inventors: Thomas J. Fogarty, Portola Valley; George D. Hermann, Los Gates, both of CA (US)

(73) Assignee: General Surgical Innovations, Inc., Norwalk, CT (US)

( * ) Notice: Subject to any disclaimer, the term of this patent is extended or adjusted under 35 U.S.C. 154(b) by 0 days.

(21) Appl. No.: 09/693,397

(22) Filed: Oct. 20, 2000

Related U.S. Application Data

(63) Continuation of application No. 09/350,809, filed on Jul. 9, 1999, now Pat. No. 6,240,924, which is a continuation of application No. 08/480,796, filed on Jun. 7, 1995, now Pat. No. 5,979,452.

(51) Int. Cl.[7] .............................................. A61B 19/00
(52) U.S. Cl. ...................................... 128/898; 606/190
(58) Field of Search ................................ 128/898, 892; 606/190, 192; 604/96–99, 104

(56) References Cited

U.S. PATENT DOCUMENTS

| | | | |
|---|---|---|---|
| 4,271,839 A | 6/1981 | Fogarty et al. | 606/194 |
| 4,469,100 A | 9/1984 | Hardwick | 604/96 |
| 4,479,497 A | 10/1984 | Fogarty et al. | 606/194 |
| 4,493,711 A | 1/1985 | Chin et al. | 604/271 |
| 5,041,089 A | 8/1991 | Mueller et al. | 606/194 |
| 5,074,845 A | 12/1991 | Miraki et al. | 606/194 X |
| 5,123,428 A | 6/1992 | Schwarz | |
| 5,163,949 A | 11/1992 | Bonutti | 606/192 |
| 5,307,814 A | 5/1994 | Kressel et al. | 606/192 |
| 5,328,469 A | 7/1994 | Coletti | 606/194 |
| 5,373,840 A | 12/1994 | Knighton | 128/4 |
| 5,439,447 A | 8/1995 | Miraki | 606/194 X |
| 5,458,572 A | 10/1995 | Campbell et al. | 606/194 X |
| 5,593,418 A | 1/1997 | Mollenauer | 606/192 |
| 6,240,924 B1 * | 6/2001 | Fogarty et al. | 128/892 |

OTHER PUBLICATIONS

Couto, J., Baptista, A., "Letters to the Editor: Endoscopic ligation of perforator leg veins" The Lancet, v337, n8755, p1480.*

* cited by examiner

Primary Examiner—Corrine McDermott
Assistant Examiner—Thomas Barrett

(57) ABSTRACT

A method of exposing, ligating, and dividing perforating veins endoscopically using balloon dissectors to gain access to the perforating veins thereby avoiding large incisions required in the Linton procedure and similar open surgical procedures.

20 Claims, 12 Drawing Sheets

Prior Art

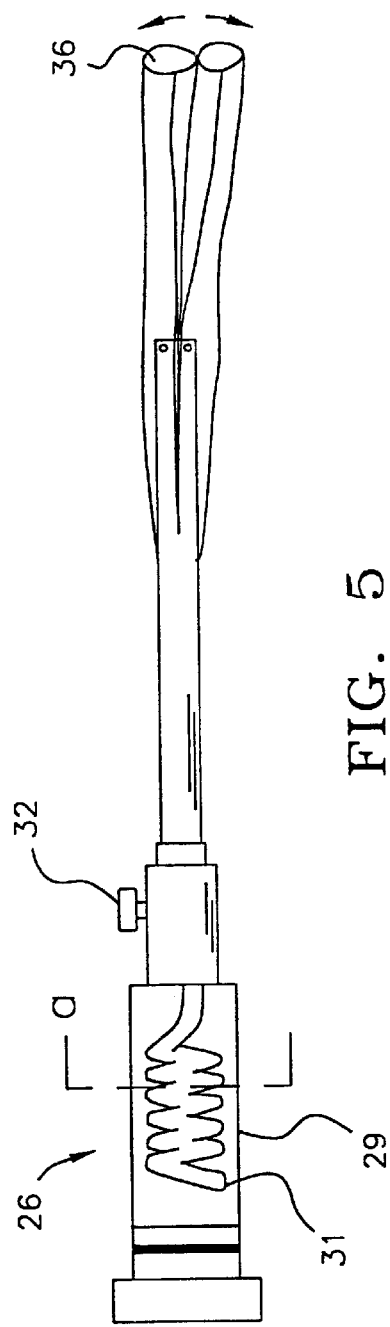
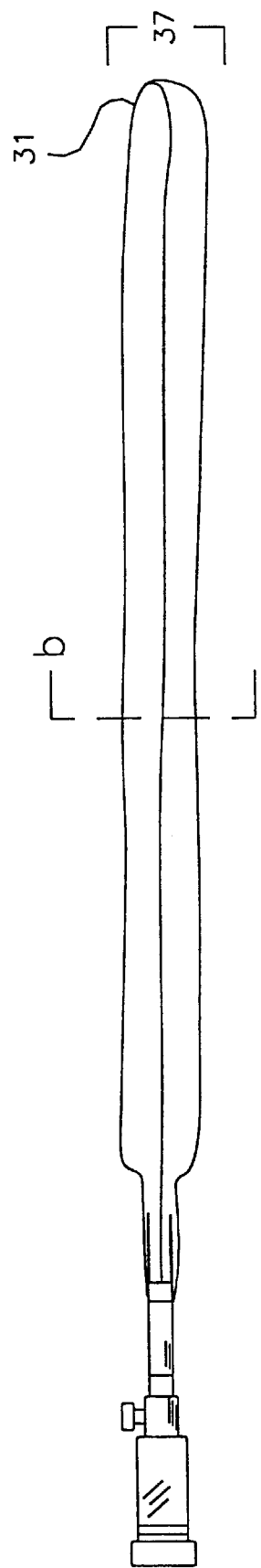
FIG. 5
FIG. 6

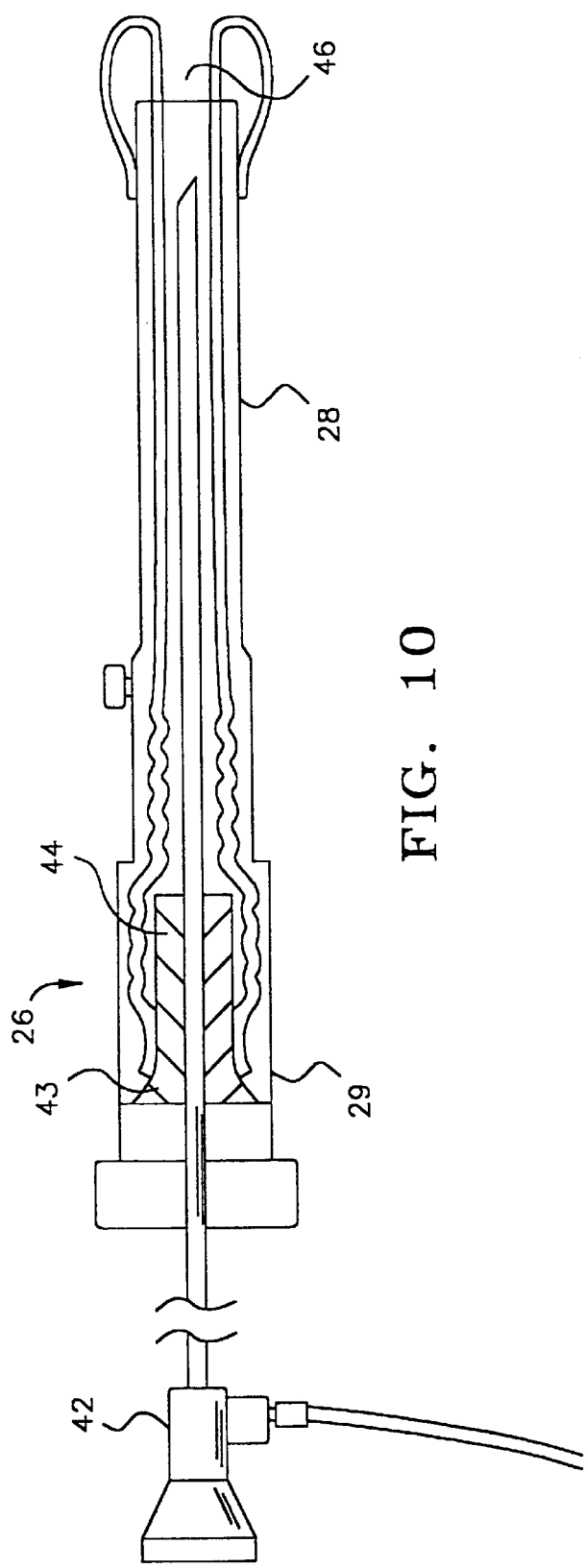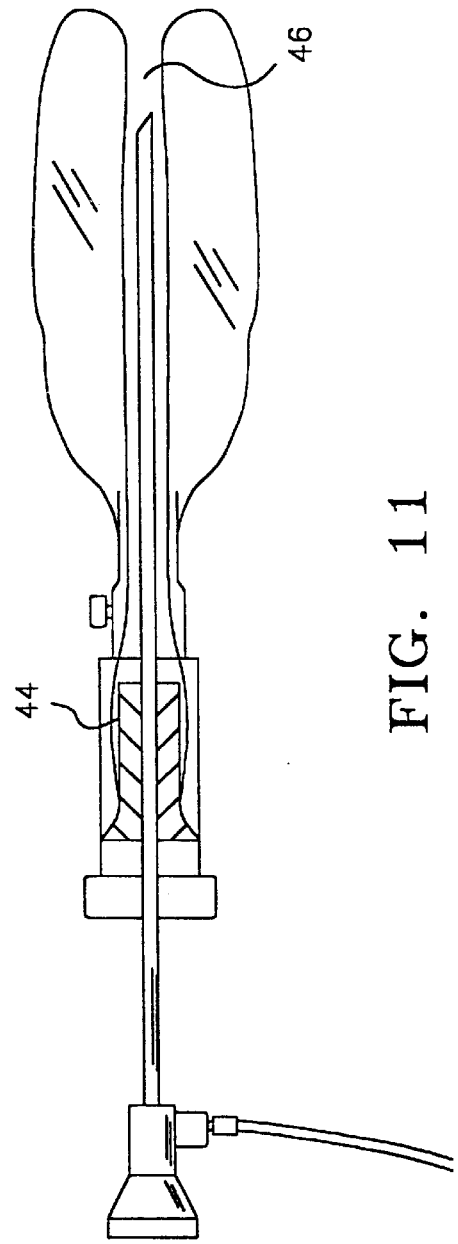
FIG. 10
FIG. 11

ENDOSCOPIC LINTON PROCEDURE USING BALLOON DISSECTORS AND RETRACTORS

CROSS REFERENCE TO RELATED APPLICATIONS

This application is a continuation of U.S. patent application Ser. No. 09/350,809, filed Jul. 9, 1999 now U.S. Pat. No. 6,240,924, which is a continuation of U.S. patent application Ser. No. 08/480,796, filed on Jun. 7, 1995, now U.S. Pat. No. 5,979,452. The priority of these prior applications is expressly claimed and their disclosures are hereby incorporated by reference in their entirety.

FIELD OF THE INVENTION

This invention relates to vascular surgery and minimally invasive surgery.

BACKGROUND OF THE INVENTION

May people suffer from varicose veins and skin ulcers which are caused by venous insufficiency. The condition usually afflicts older people, and is most evident in the lower legs, and is evident in may people as large bumpy veins showing through the skin, discolored skin around the ankles, and open sores on the inside of the ankle. The condition is painful and disabling.

Venous insufficiency is often caused by failure of the valves located in small communicating veins which connect large superficial veins such as the posterior arch vein or saphenous vein, with large deep veins such as the peroneal or tibial veins. The communicating veins have valves which look like duckbill valves or leaflet valves that act as check valves, allowing blood to flow from the superficial veins into the deep veins, but blocking flow in the reverse direction. Exercise and movement of the calf muscles around the communicating veins squeezes blood through the communicating veins. This mechanical pumping action, combined with the function of the valves, is responsible for returning blood flow to the heart. When the valves fail, venous blood in the superficial veins cannot be pumped into the deeper veins, resulting in blood pooling in the legs. The condition causes very poor circulation in the legs and can lead to the varicose veins and skin ulcers. Large varicose veins in the lower leg, skin ulcers just above the ankle bone on the inside of the calf, and discolored skin on the lower leg are common symptoms. Similar symptoms are seen in other areas of the body, particularly the thighs and arms, when perforating veins in those areas become incompetent.

Venous insufficiency is generally attributed to the failure of certain groups of perforating veins. There are about 150 perforating veins in the leg, but there are several major perforating veins which are important contributors to the problem of venous insufficiency. An important group of perforators is found high on the inside of the calf, over the calf muscle. Another important group of perforators is found low on the inside of the calf, just above the ankle and toward the back of the leg. Another set of perforators which is found on the lateral or outside of the leg run through the muscles on the outside of the calf.

An effective surgical treatment of this condition was developed by Linton circa 1938. In the Linton procedure, also referred to as the Medial subfascial approach, the calf is cut open along the Linton line, extending from just above the ankle bone (or medial malleolus) on the inside or medial side of the foot, up the inside of the calf almost to the knee. The incision is deep enough to cut the skin and fat, and also the deep fascia which is a filmy fibrous layer of tissue which covers the muscles of the calf. Upon peeling away the skin, fat, and fascia, some of the communicating veins can be seen, and these are cut and tied off.

Another effective surgical treatment, similar to the Linton procedure is called the stocking seam approach. In the procedure, an incision is made along the back of the calf (where a seam would appear in an old fashioned pair of panty hose). The skin, fat, and fascia are cut and pulled away from the muscles to expose some of the communicating veins, and sometimes the large calf muscles are pulled apart to expose more communicating veins. This procedure can effectively cure the problem of venous insufficiency, provided that the major incompetent perforating veins are severed. One of the problems encountered in this therapy is that failure to sever all of the hemodynamically significant incompetent perforating veins may result in recurrence of the varicose veins and blood pooling.

Another problem encountered with the above procedures is that they require invasive open surgery with significant skin incisions which is undesirable in any case, but is particularly undesirable in cases of venous insufficiency because the poor blood flow makes it harder for the incisions to heal. Because the operation is so radical, it is often put off until the symptoms are severe. The high morbidity associated with this procedure has made it relatively unpopular, with the majority of patients with venous insufficiency opting for nonsurgical palliative treatment called compression therapy. Compression therapy is uncomfortable, lifelong, and does not correct the underlying hemodynamic pathology of incompetent venous valves. Thus, a minimally invasive procedure which requires tiny incisions far away from the ulcerated skin is desirable.

BRIEF DESCRIPTION OF THE DRAWINGS

FIGS. 2a through 3b illustrate the endoscopic operation for accessing, ligating, and dividing perforating veins of the leg.

FIG. 5 shows the balloon dissector with the balloon in its inflated state.

FIG. 6 shows the balloon dissector with the balloon fully inflated.

FIG. 10 shows a balloon dissector with a thru-lumen.

FIG. 11 shows the balloon dissector with thru-lumen with the balloon fully inflated.

DETAILED DESCRIPTION OF THE INVENTION

Figure 1:
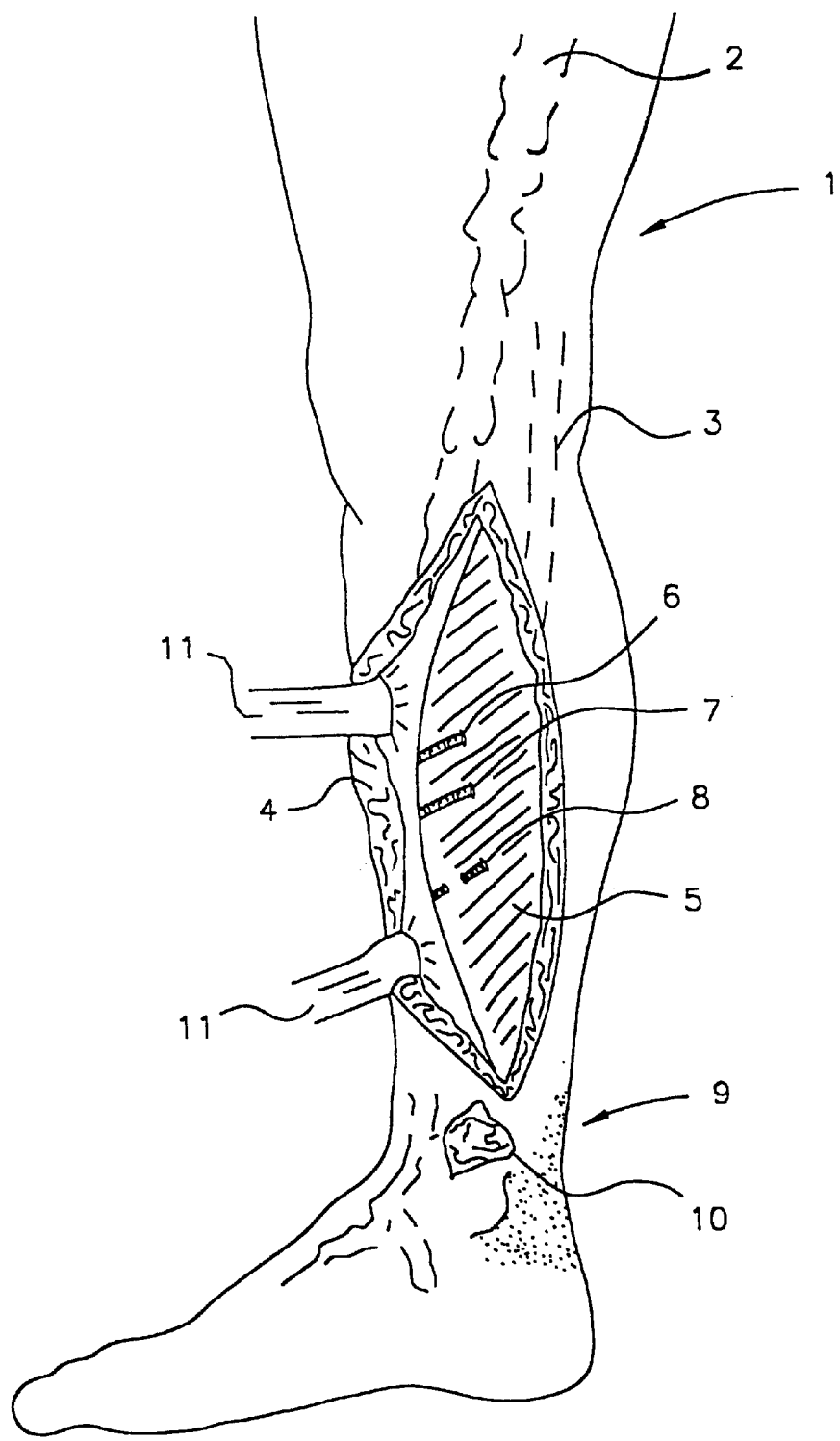
FIG. 1 and 1a are medial and posterior views of the leg showing the superficial veins, deep veins, and perforating veins of the calf.

Referring to FIG. 1, the superficial veins of the leg 1, such as the great saphenous vein 2, are close to the surface, and deep veins such as the tibial vein 3, shown in phantom, are deep within the calf under the muscles, such as the soleus or gastrocnemius muscles. The saphenous vein runs through the fat layer 4 and the above deep fascia 5. Occasional perforating veins 6, 7, and 8 connect the saphenous vein with the deep tibial vein. The perforating veins pass through the deep fascia and muscles of the leg to reach the deep veins. When the perforating veins fail to block retrograde flow from the deep tibial vein to the superficial veins, the superficial veins become varicose, and the skin becomes discolored in the ankle region 9 shown by mottling, and a skin ulcer 10 may form.

FIG. 1 serves to show the anatomy of the perforating veins and to illustrate the Linton procedure. In the Linton procedure, the leg is cut open along the Linton line which extend from the ankle to the inside tope of the calf. As shown in FIG. 1, the perforating veins enter (or perforate) the deep fascia 5 just under the skin and fat. The skin and fat have been cut away and pulled away with retractors 11. FIG. 1 shows three perforating veins in this area of the leg, but there may be more or less (it varies from person to person). The perforating veins are identified as the veins that run into the deep fascia, as illustrated. Numerous other veins running through the fat are distinct from the perforating veins because they do not pass through the deep fascia. The perforating veins are cut and tied off, or clipped, as shown in regard to the lowest perforating vein 8. After all the exposed perforating veins are ligated and divided, the leg is sutured closed. If all the incompetent veins were identified and severed, the varicose veins, discolored skin, and skin ulcers caused by the condition should eventually subside because the circulation in the leg improves after the operation.

Figure 2:
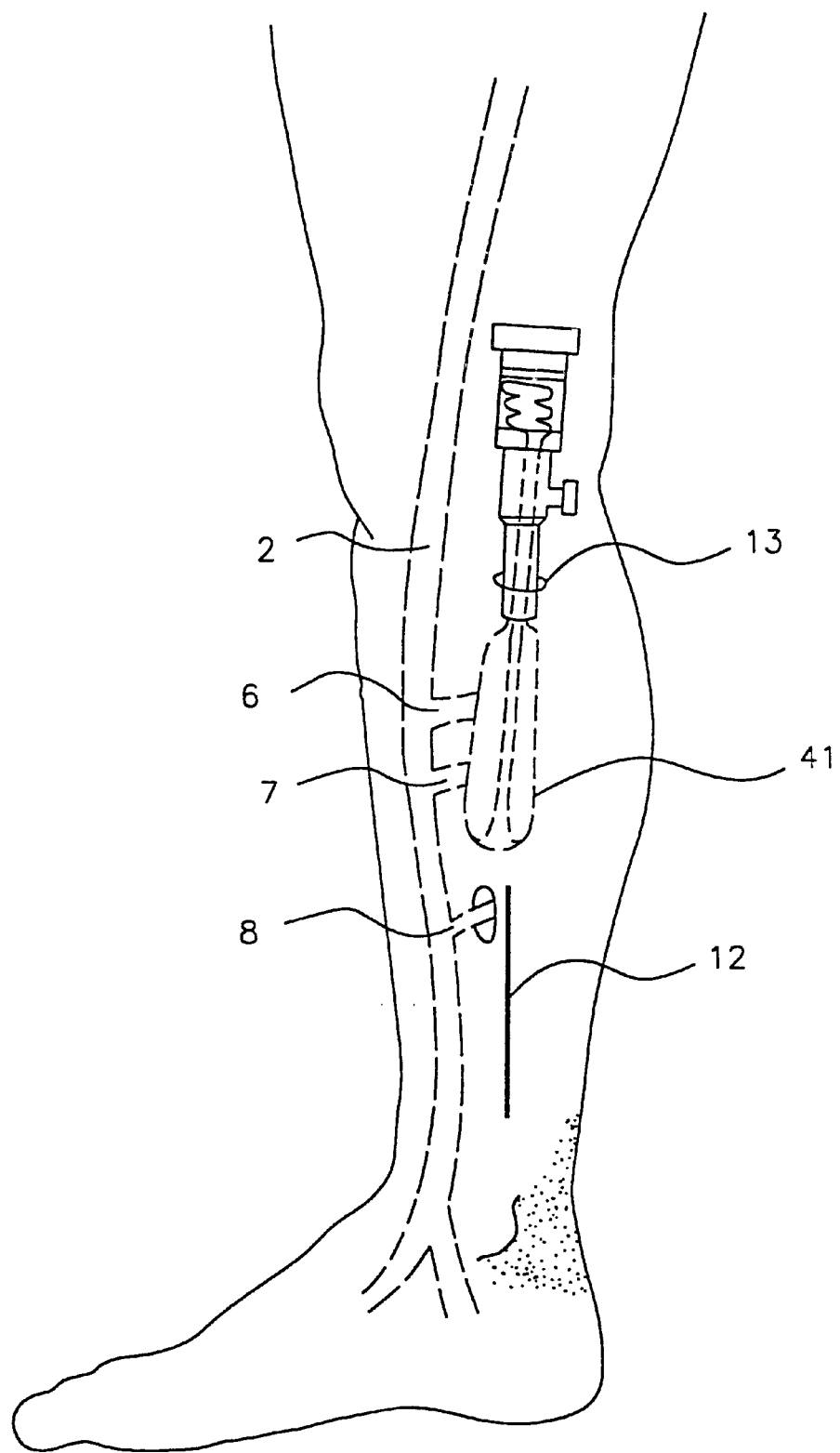
FIG. 2 is a view of the balloon dissecting device inserted in the calf.

The Linton procedure accomplished using the balloons of the present invention is illustrated in FIG. 2. The balloon is inserted high on the calf, on the inside or medial part of the calf, in an area corresponding to the high end of the Linton line shown in FIG. 2 as item 12, about 10–15 cm below the knee. Only a small incision or cutdown 13 is necessary, and this incision need be only about 2 cm long. Any one of the balloon dissecting devices described in detail below is inserted into the incision, and pushed just a short distance downward along the Linton line, between the deep fascia and the muscle. The everting balloons are inflated to cause them to evert or unfold, and they push their way along the Linton line, along the anatomical plane defined by the boundary between the deep fascia and the muscle. The noneverting balloons are merely pushed along the Linton line, along the tissue plane between the fat and deep fascia. The perforating veins should be the only significant veins which pass through this tissue plane. (The balloon dissectors may also be inserted between the fat and the deep fascia to uncover the perforating veins, but this approach may also uncover various nonperforating tributary veins running though the fat layer). In this manner, the balloons dissect the deep fascia layer from the muscle to "uncover" the perforating veins in the tunnel shaped working space created by the dissection. The balloons may be guided from the outside by pushing on the skin near the tip of the balloon as it propagates down the leg. The balloon passes by the communicating veins 6, 7, and 8 as shown in phantom in FIG. 2.

Figure 3:
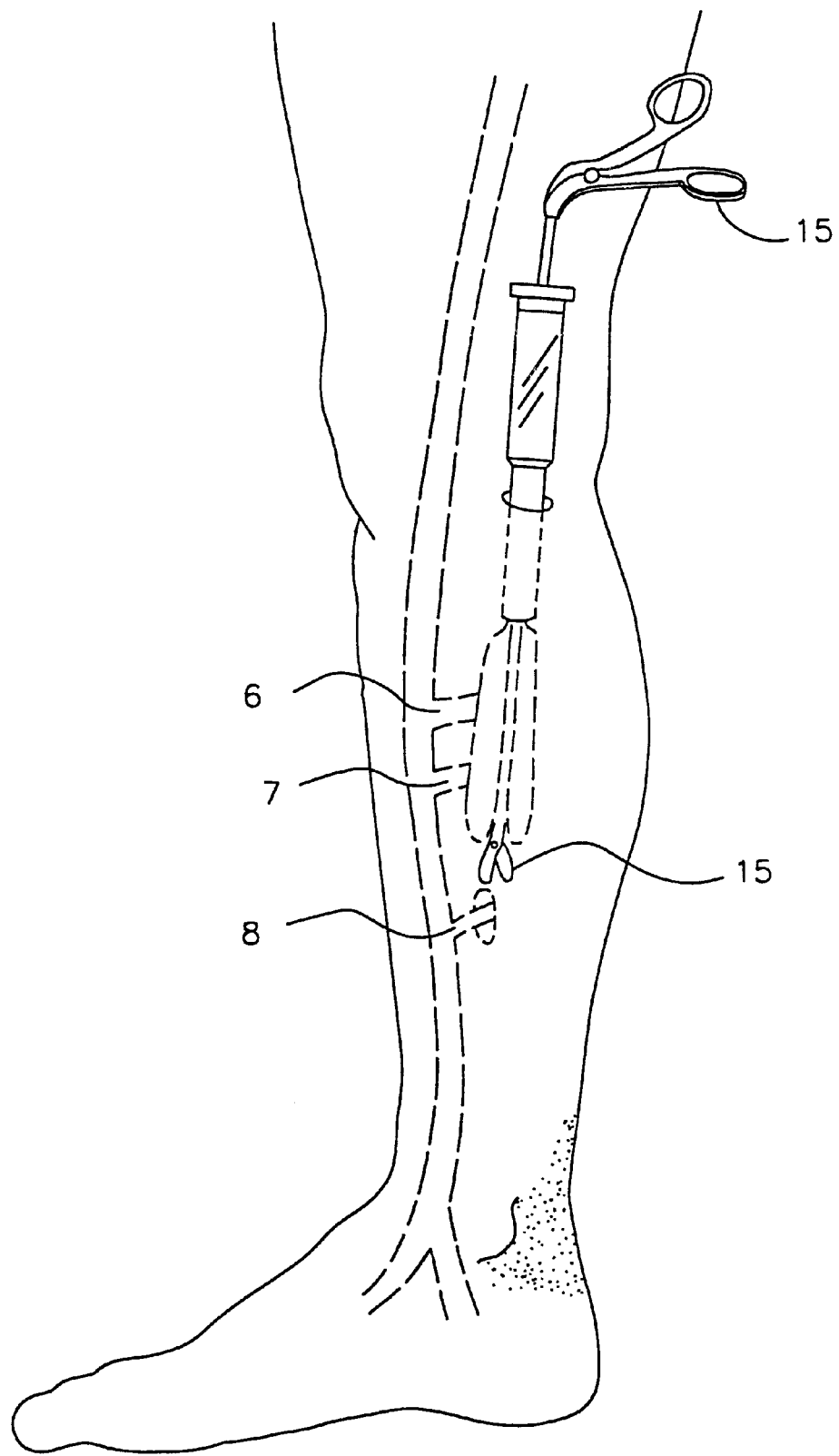
FIG. 3 is a view of one embodiment of the balloon dissecting device inserted in the calf.
Figure 3A:
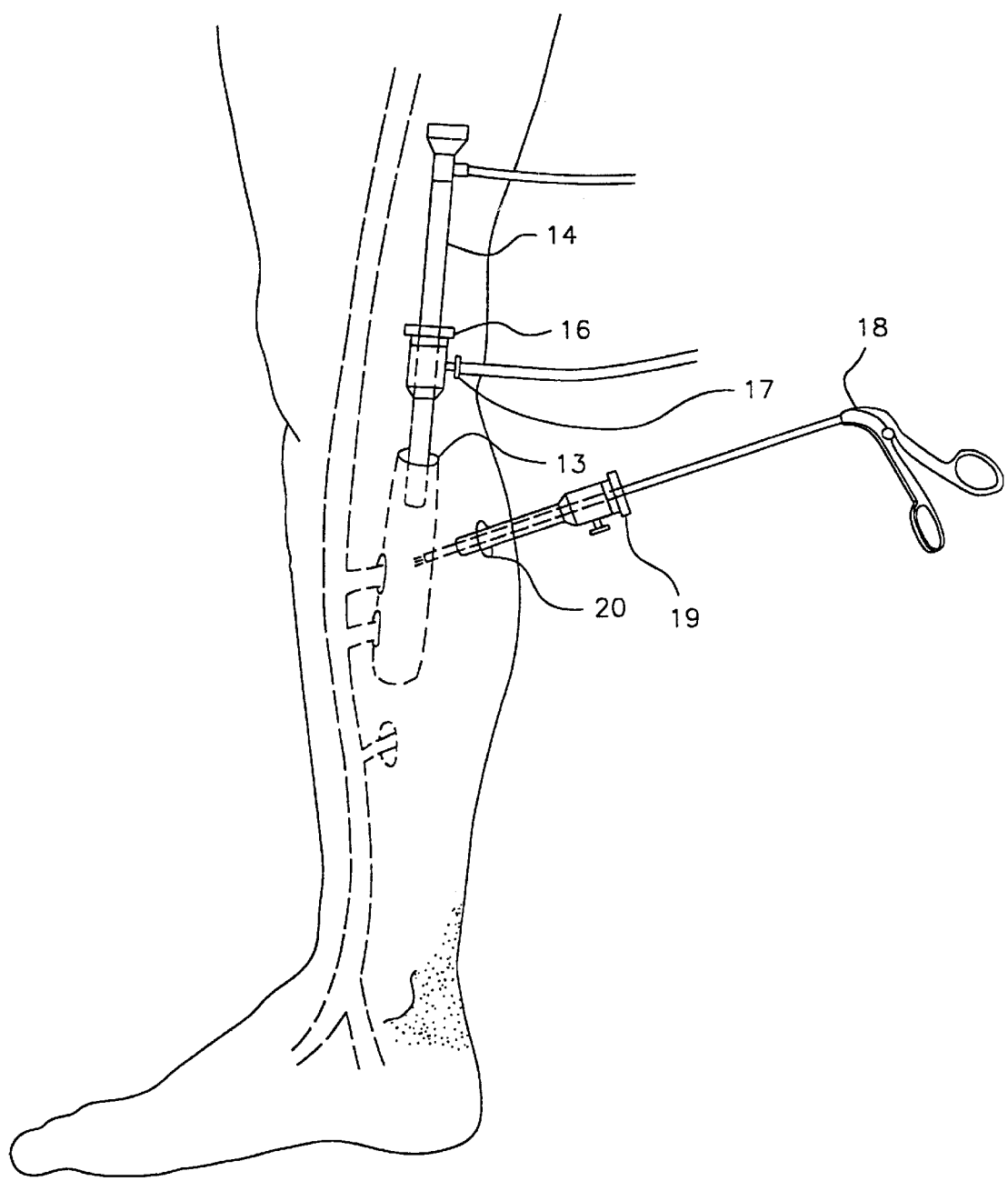

Insertion of the balloons creates a long tunnel shaped working space over the communicating veins. The veins may be divided and ligated as they are encountered by the balloons. This procedure is facilitated by use of one of the balloons with a central lumen. As shown in FIG. 3, the balloon dissecting device of FIG. 11 (for example) which has a central lumen, is inserted into cutdown 13 and inflated to propagate along the Linton line towards the ankle. The balloon encounters various perforating veins, and these may be seen through an endoscope 14 inserted through the central lumen of the balloon dissector. As each perforating vein is encountered, it may be clipped and cut with tools inserted through the central lumen of the balloon. FIG. 3 shows an endoscopic cutter 15 disposed within the central lumen of the balloon. The cutter may be inserted along with an endoscope or endoscopic clip applier.

Figure 3B:
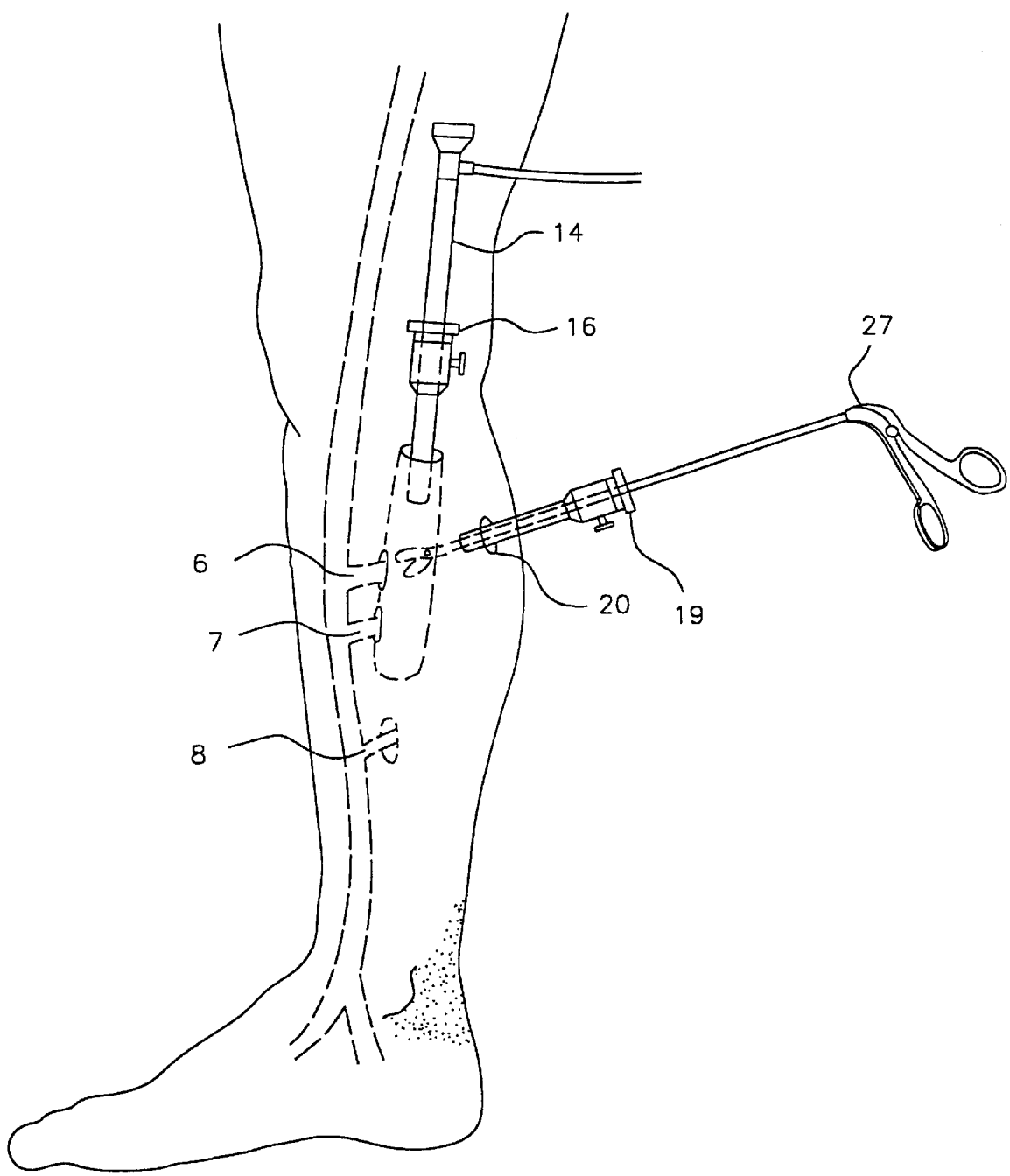

It may be desired to insufflate the tunnel created by the balloon before ligating and dividing the communicating veins. To accomplish the procedure with insufflation as illustrated in FIGS. 3 through 3b, the balloon dissector is inflated to dissect along the plane dividing the skin and deep fascia, and it creates a tunnel. The balloon is deflated and removed, and a cannula 16 is placed in the small incision 13 in its place. The tunnel created by the balloon is insufflated (inflated) through the inflation port 17 on the cannula, and this creates a long inflated tunnel. When the tunnel is sufficiently inflated, an endoscope 14 and an endoscopic clip applier 18 can be inserted into the leg via the cannula. As illustrated, the clip applier is inserted through a second access port with second cannula 19 inserted into the insufflated work space through second cut down 20, and a clip applier is inserted through the second cannula. The clip applier is used to place two clips on each perforating vein to ligate each one. After the veins are clipped, the clip applier is removed and, as shown in FIG. 3b, an endoscopic cutter 21 is inserted into the leg to cut the veins, cutting each perforating vein between the clips. The clip applier and cutter may be inserted through the same cannula 16 as is used for the endoscope. Alternatively, as shown the clip applier and cutter may be inserted through a second endoscopic access port inserted into the insufflated tunnel at a convenient point below the first incision.

After the perforating veins are cut, the cutter, endoscope, and the cannulas are removed from the leg, and the small incision is stitched closed. Only the small incision is left to be sutured, and it is high on the calf in an area not usually affected by the poor circulation and ulceration seen low in the calf, so that the wound heals faster and with less complications than the large wound in the normal Linton procedure.

Where the balloons having central lumens described below are used to create the tunnel, the procedure may be simplified over the procedure described above. As these balloons dissect along the fat/deep fascia plane to uncover the perforating veins, an endoscope or laparoscope may be placed in the central lumen of the balloons to search for perforating veins as they are encountered by the balloon. Because the balloon dissector has a substantial diameter and thickness, the balloon raises the fat and skin from the deep fascia and creates a workspace at the distal tip of the balloon. The workspace will accommodate the endoscopic clip appliers and cutters necessary for the procedure. The lumen passing through the center of the balloon may accommodate endoscopic instruments in addition to the endoscope so that a clip applier may be inserted into the workspace alongside the endoscope to place clips on the veins and a cutter may be inserted into the workspace through the same lumen to cut the veins while the operations are viewed through the endoscope. When the communicating veins are ligated and divided, the instruments are removed, the balloon is deflated and removed, and the small incision is stitched closed.

Figure 1A:
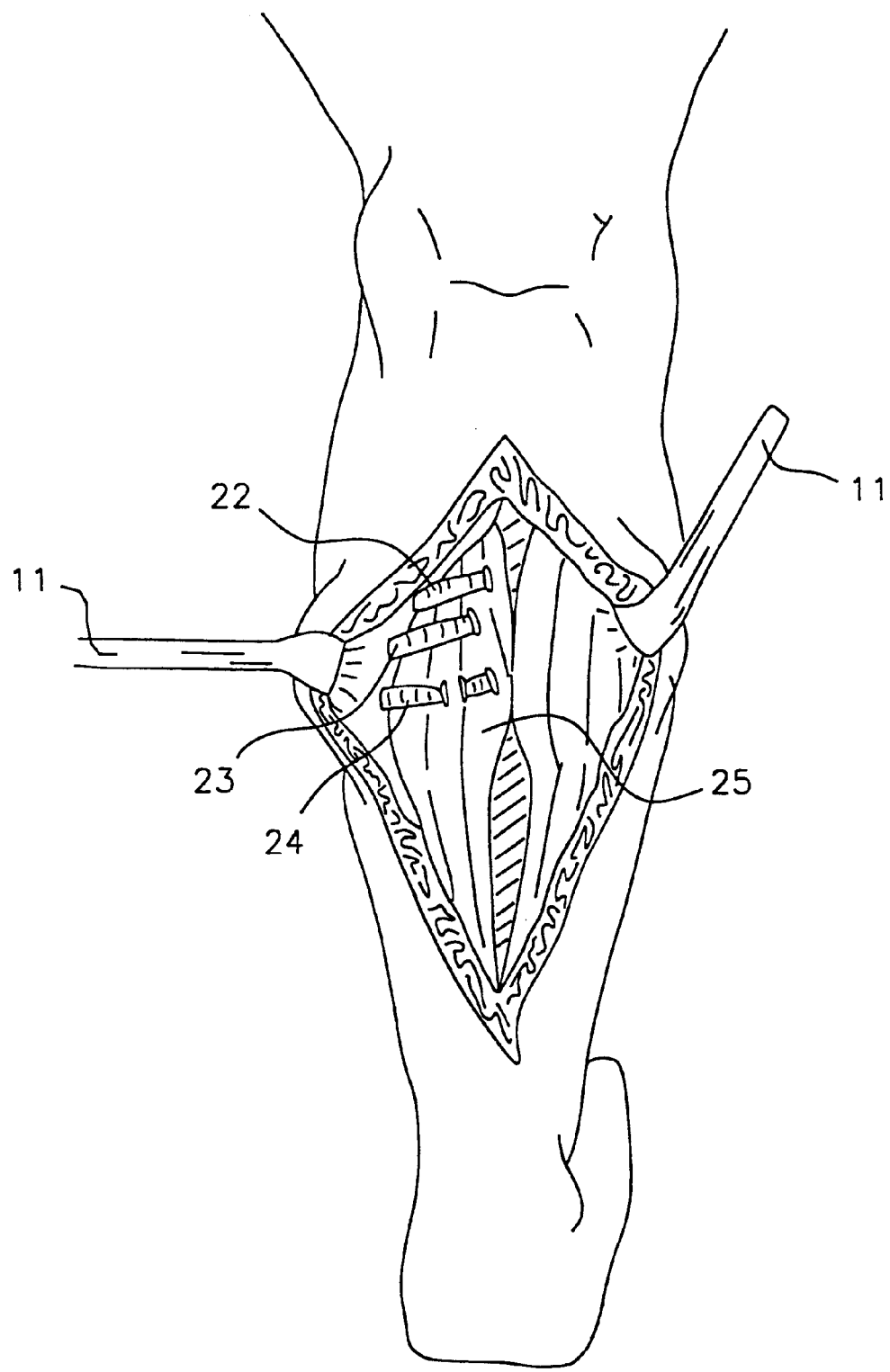

It should be appreciated that several other standard procedures for dividing and ligating perforating veins can be accomplished with the balloon devices, and the medial subfascial approach illustrated in FIG. 1 is but one example of surgical treatments for venous insufficiency. Another approach is illustrated in FIG. 1a, which shows the stocking seam approach. This approach is used to gain access to the communicating veins near the inside of the ankle and also to gain access to communicating vein on the outside or lateral side of the calf. In the stocking seam approach, the calf is cut along the back or posterior surface. The skin incision reached from just below the crease of the knee (the popliteal crease) to just above the ankle. The skin and fat are pulled away with refractors 11 to expose additional communicating veins 22, 23, and 24 which enter the deep fascia near the gastrocnemius muscle 25. These veins are clipped and cut to accomplish the procedure.

This stocking seam approach can be accomplished endoscopically in the same manner as the Linton procedure. The large incision shown in FIG. 1a can be replaced with a small 3 cm incision near the top posterior surface of the calf, and the perforating veins 22, 23, and 24 can be exposed using the balloon methods described above to dissect the skin, fat, and deep fascia away from the deeper body tissue and muscle and creating an endoscopic working space. Endoscopic tools are then used to ligate and divide the communicating veins in the same manner as described above.

Figure 4:
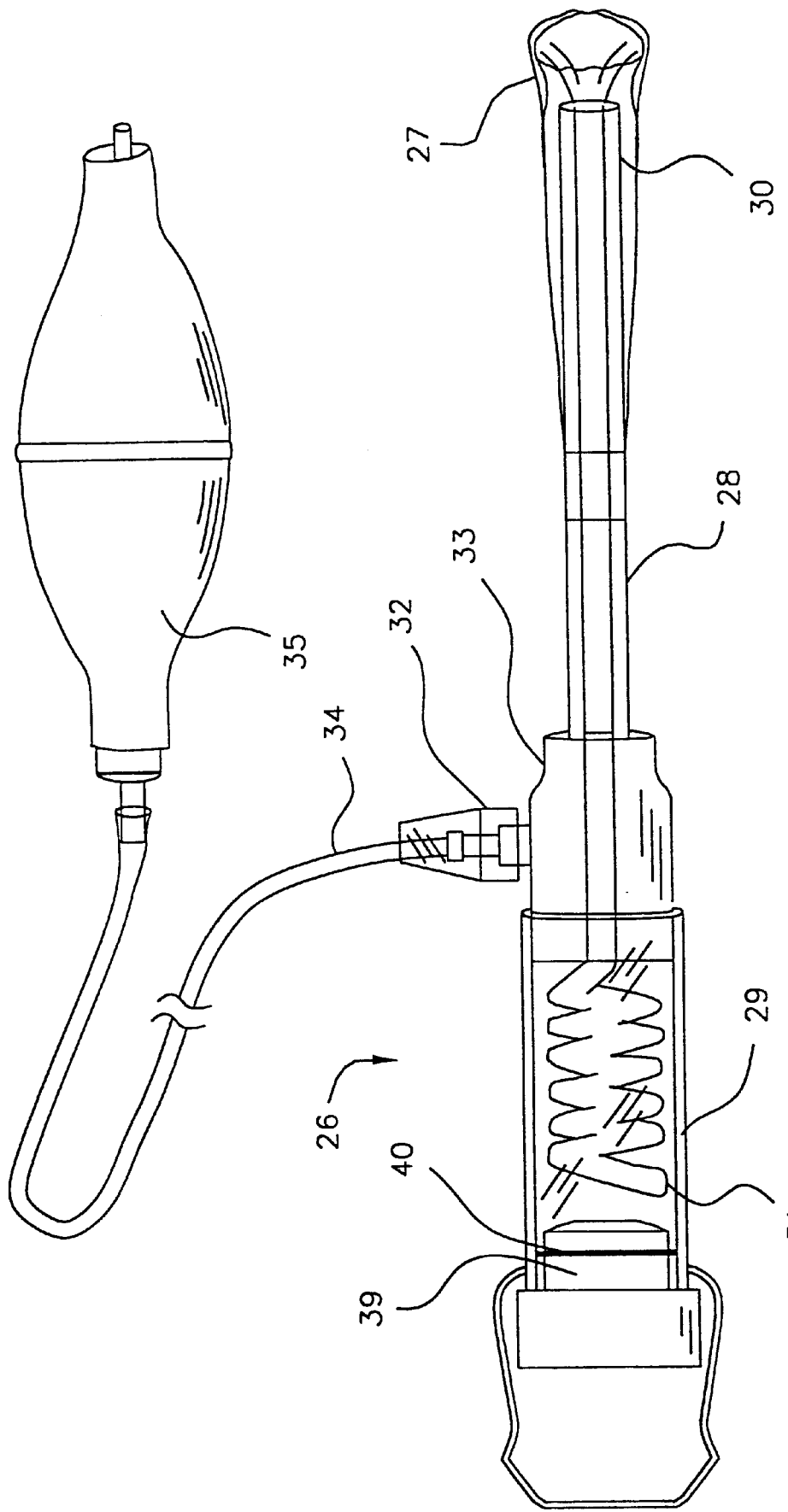
FIG. 4 shows the balloon dissector with the balloon housed in the handle.

The balloons to be used in the endoscopic Linton procedure described above are illustrated in the remaining figures. FIG. 4 shows the balloon dissector or balloon trocar 26 in its uninflated state, with the balloon packed inside the device. The balloon 27 is a nonelastic balloon or bladder. The balloon trocar 26 comprises a balloon 27, a trocar portion 28, and a balloon housing portion 29. The trocar portion is cylindrical, with a circular cross section, but may be made in oval cross section or in other cross sections. The balloon is sealed to the distal tip 30 of the trocar portion 28 of the balloon trocar 26. The balloon material is wrapped over the distal tip 30 and sealed to the outside of the trocar portion 28. The balloon may be sealed to the trocar with adhesives, or it may be heat sealed, banded, taped (cellophane tape, such as Scotch™ tape, is sufficient), or sealed in any suitable manner to the trocar. The balloon then extends back through the trocar, to the proximal balloon housing portion 29 of the balloon trocar 26. When used for tunneling along the saphenous vein, the balloon is approximately 60 centimeters long. The trocar or cannula is most conveniently 10–20 centimeters long so that the excess length of the balloon is folded as shown inside the balloon housing portion of the balloon trocar. The balloon is sealed at its distal end 31, referring here to the distal end as determined when the balloon is everted outside of the balloon housing. The balloon may be formed by extrusion or by heat sealing or gluing a number of pieces of material together.

The balloon trocar 26 is fitted with an inflation port 32 which may be located anywhere on the trocar portion or balloon housing. In FIG. 4, the inflation port is shown affixed to the balloon housing at its proximal end near the neck-down portion 33 between the balloon portion and the trocar portion. The inflation port comprises a tube establishing a pathway for fluid or gas to be injected into the balloon trocar to inflate the balloon. A convenient length of tygon tubing 34 connects the balloon to a bladder pump 35 or large syringe capable of injecting fluid or gas into the balloon housing. Sterile saline solution is the preferable inflation medium for medical applications. Alternately, air, $CO_2$, or even foam or other substances may be injected to cause inflation.

Upon injection of fluid or gas into the balloon housing, the pressure created inside the housing forces the balloon to evert out through the trocar portion of the balloon. The segment of the balloon stored in the housing portion gradually rolls forward (distally) and outside the trocar, rolling over itself and turning itself inside out, or everting, and pushing forward. As shown in FIG. 5, the balloon has everted under pressure, and the leading edge 36 pushes forward through body tissue. Eventually the balloon completely unfolds or everts to create a long cylindrical balloon. The balloon may be folded in a variety of ways, including the fan fold shown in FIG. 5, or with accordion folds as shown in FIG. 11, or it may be rolled inside the cannula.

Figure 7:
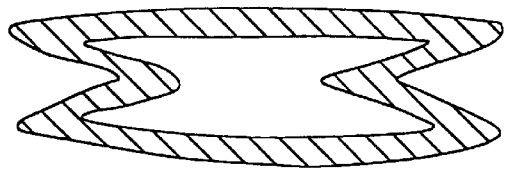
FIG. 7 shows a cross section of the inflatable membrane in its uninflated state.
Figure 8:
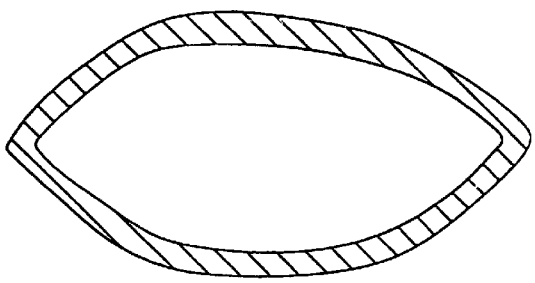
FIG. 8 shows a cross section of the inflatable membrane in its inflated state.

The fully inflated and everted balloon is showed in FIG. 6. The inflated diameter of the balloon is larger that the diameter of the trocar. This allows for the creation of a tunnel that is wider than the trocar. The balloon diameter or radial cross section of the balloon may also be smaller than the diameter of the trocar and may be adjusted to create a tunnel of any desired size. The balloon may be pleated, or folded like a brown paper bag, to facilitate eversion and packing in the housing. The cross section of the uninflated balloon along section a of FIG. 5 is shown in FIG. 7, and the cross section of the inflated balloon along cross section b of FIG. 6 is shown in FIG. 8. The balloon is preferably nonelastic so that it will not expand uncontrollably into the softest body tissue or weakest tissue plane. Acceptable materials include polyethylene and other medical grade plastics. A slight degree of elasticity is acceptable, and even complete elasticity may be acceptable where there is no danger of the balloon expanding in an unwanted or unpredictable shape.

Figure 9:
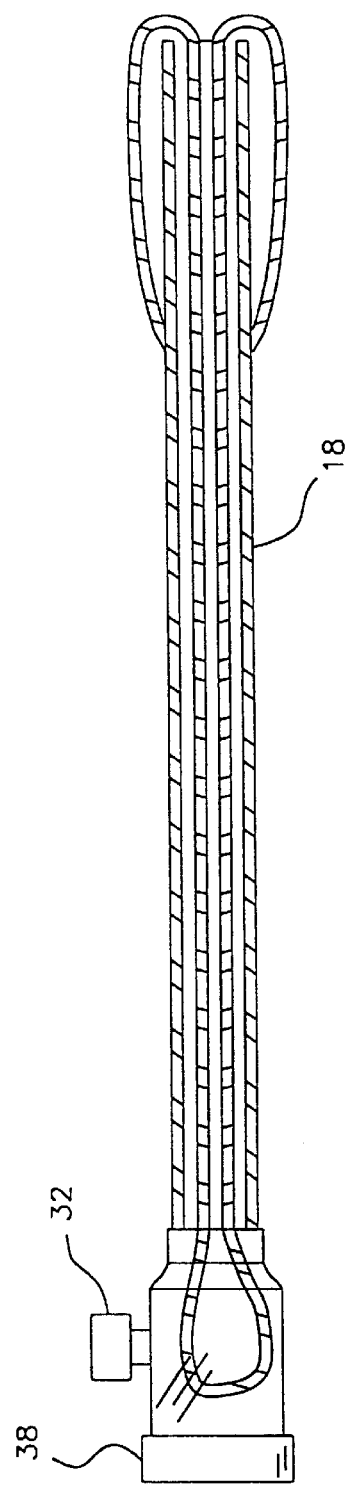
FIG. 9 shows a cross section of a simplified balloon cannula.

FIG. 9 shows an alternate embodiment of the balloon trocar in which the excess length of the balloon is stored inside a longer housing so that it need not be folded. The balloon housing 18 is longer than the balloon housing 18 shown in FIG. 4. The balloon is sealed at the distal tip of the trocar in the same manner shown in FIG. 4, and the distal end of the balloon is sealed. The inflation port 32, again, may be placed in any convenient place on the balloon trocar. The proximal end of the balloon housing is sealed by an end cap 38 which can be integrally formed with the balloon trocar. The end cap can also be removable and include a threaded cap which is screwed onto the end of the balloon housing and fitted with a gasket to prevent leakage. The end cap can also include a plug 39 which fits tightly into the balloon housing, and the plug may be provided with an O-ring 40 to help maintain the seal on the housing. Upon inflation, the balloon everts or unfolds out the distal tip of the balloon trocar. The balloon forces itself between the body tissues to be dissected or tunneled through in the same manner as described above.

FIG. 2 shows the balloon trocar inserted into the ankle incision or cut down 13. The surgeon inserts the balloon into the incision and points it in the direction of the tunnel that he wants to make. In the illustration, the balloon trocar is inserted as it would be if the surgeon wanted to create or enlarge a tunnel along the Linton line. Once the surgeon has put the balloon trocar in place, the balloon is ready for inflation. The surgeon can inflate the balloon and allow it to evert into the leg. The balloon will follow a tunnel previously created by the surgeon with a blunt dissecting tool, if the surgeon has chosen to create the tunnel with another tool and use the balloon to enlarge that tunnel. The balloon will also create its own tunnel without the need to create an initial tunnel along the Linton line. The surgeon can make a small starter tunnel, using a finger or tool to get the tunnel started, then the surgeon can insert the balloon and inflate it. Upon eversion or unrolling, the balloon will force its way into the leg and propagate along the tissue boundary between the muscle and deep fascia. Eversion and propagation of the balloon creates a tunnel under the fascia. As the balloon propagates along the Linton line, it raises the skin over the balloon, creating a bubble or blister 41 which indicates that the balloon is everting along the Linton line, and not taken some errant course. As the balloon propagates down the leg, the surgeon may guide it by pushing the tip of the balloon with his finger, through the skin without puncturing the skin. In this manner, the balloon gently forces its way between the layers of body tissue and pushes them apart to form the enlarged tunnel necessary for endoscopic surgery on the perforating veins.

As described above, the balloon trocar is used for dissection or tunneling in a semi-blind manner. When used in the leg, the propagation of the balloon can be observed by watching skin rise as the balloon tunnels under the skin. Because the location of the perforating veins are well known, the surgeon can be sure that the balloon is following the intended path along the Linton line. In some cases, however, the surgeon may wish to observe the propagation of the balloon endoscopically, or the surgeon may wish to observe various structures as the balloon everts past the structures. The everting balloon with a thru-lumen depicted in FIG. 11 can be used in this instance.

Figure 12:
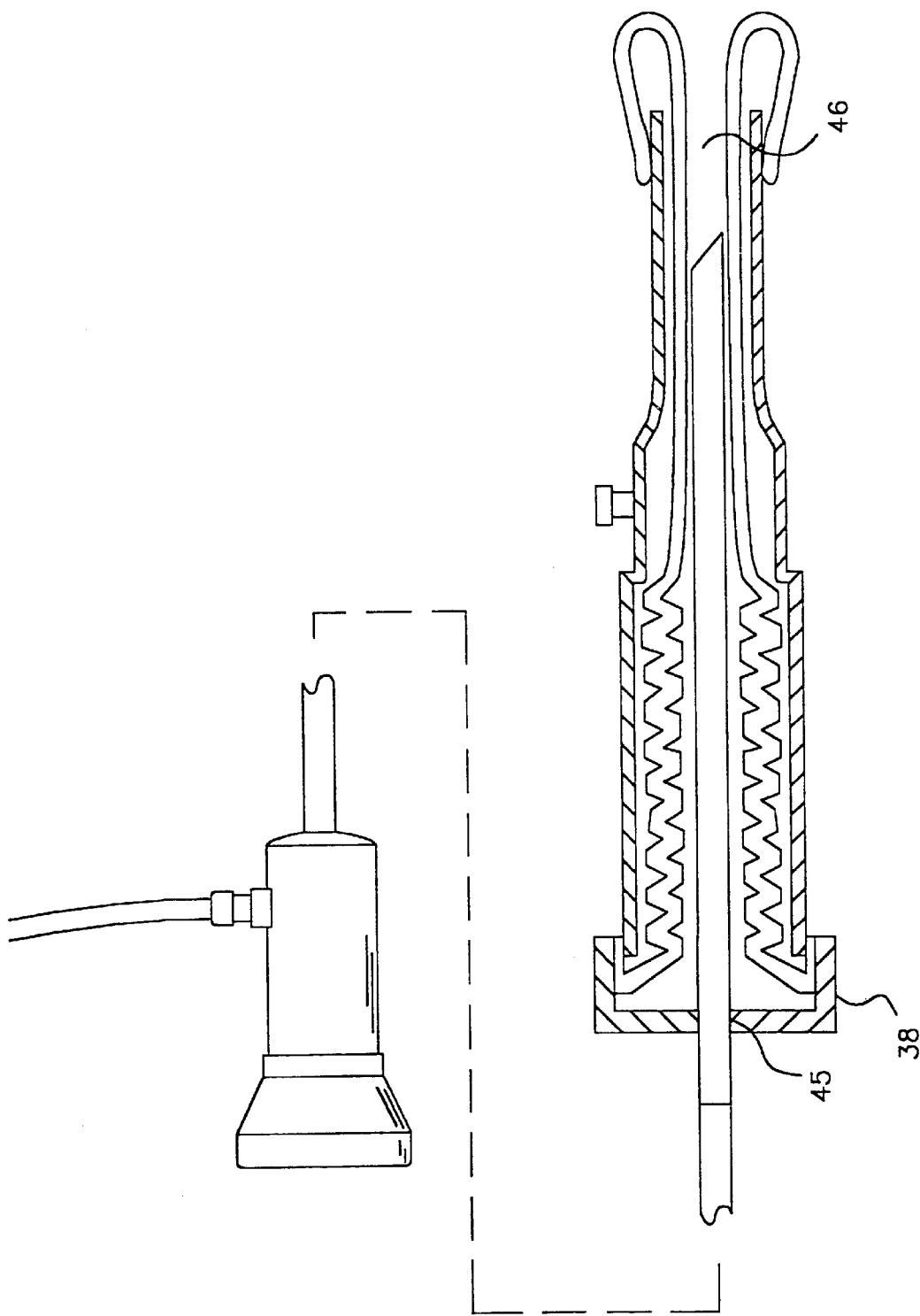
FIG. 12 shows an alternative embodiment of the balloon dissector with a thru-lumen.

As shown in FIG. 10, the balloon trocar 26 may be constructed to allow passage of an endoscope 42 or other instrument through the balloon. The balloon housing 29 and trocar portion 28 of the device may be similar to the comparable structures shown in FIG. 4. The balloon is sealed to the distal tip of the trocar portion and is also sealed to the proximal end of the balloon housing by sealing the balloon to the sliding piston seal or sliding plunger 43. The sliding piston seal fits tightly against the inside of the balloon housing to create an air tight seal. A guide tube 44 is provided attached to the sliding piston to facilitate sliding the laparoscope through the through lumen. Alternatively, in the configuration shown in FIG. 12, the balloon comprises a tube of nonelastic material with a short length of cuff rolled back at each end and folded over the proximal edge and sealing it to the outside of the balloon housing. The balloon housing may be provided with an end cap 38 to prevent backward eversion of the balloon, and the end cap may be provided with a port 45 which accommodates the laparoscope. Any other suitable sealing means may be used. FIG. 11 shows the balloon in its fully extended state with the lumen large enough for a laparoscope to be inserted through the inside of guide tube or mandril 44. With the balloon inflated or deflated, a laparoscope can be inserted through the through-lumen 46, as shown in FIGS. 11 and 12.

Before the balloon is inflated to cause eversion which is used for tunneling or dissection or retraction of body tissue, it is folded accordion style inside the balloon housing portion of the balloon trocar. The excess length is held inside the housing in this manner until the balloon is everted under pressure. The accordion folds 47 can be made without a mandril, as shown in FIG. 12, or with a mandril 44 as shown in FIGS. 10 and 11. Alternatively, the laparoscope or other instrument used within the lumen may be used as the mandril. The mandril can be integral with the end cap, or it can be mounted on a fixed or sliding plunger, annular seal, sealing ring, or piston seal 32. Provision of a sliding plunger allows longer deployment of the balloon outside the trocar portion.

While in use, the balloon may be inflated and everted partially or fully to cause it to tunnel through body tissue or between tissue planes. During eversion, the laparoscope can be advanced to the leading edge or everted distal end of the balloon so that the surgeon can view the body tissue as it is dissected.

Figure 13:
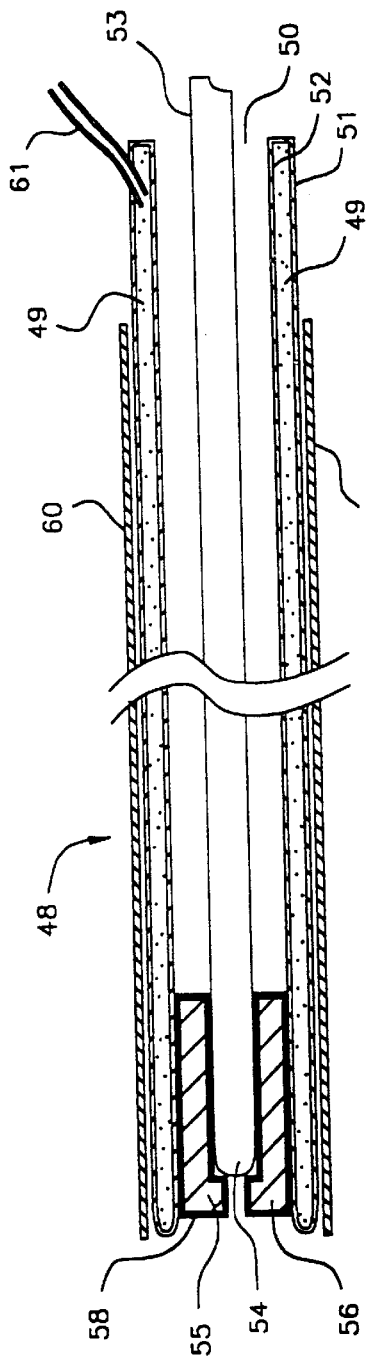
FIG. 13 shows a balloon loaded blunt dissector for use with the procedure.

FIG. 13 shows an embodiment of the balloon loaded-blunt dissector 48 in its uninflated state, with the balloon packed inside the device. The balloon 49 is a nonelastic balloon or bladder and is cylindrical or tubular with a central lumen 50. The balloon has two walls 51 and 52 and may be described as a double walled balloon tube. The balloon may be made of polyethylene, polyurethane, polyimide, and other nonelastic materials, as well as latex and other elastic materials. The balloon may be any suitable length, for example 12 to 24 inches long, to provide a tunnel of convenient length when exposing the perforating veins, and the balloon may be any convenient diameter or width, for example 2 to 3 inches, to allow for laparoscopic instruments to fit and operate conveniently within the tunnel created by the balloon. The balloon tube may have a suitable cross section.

A guide rod 53 with a blunt or rounded tip 54 is disposed in the central lumen of the double walled balloon tube. The guide rod is used as a pushing member to push the balloon through body tissue. A support tube 55 may be provided to give some columnar support for the device and provide a stop member or coupling member to translate pushing force on the guide rod to pushing action on the balloon tube, and the tube may have an overhanging lip 56 which obstructs passage of the guide rod or endoscope, or the guide rod or endoscope can be fitted with a stop collar 57 to engage the support tube. The support tube may have a square tip 58 as in FIG. 14 or a rounded tip 59 as in FIG. 15. The guide rod and support tube are used to push the balloon along the saphenous vein or other desired pathway between dissectable tissue layers. The balloon tube is illustrated as separate from the guide tube and endoscope which provides for use with fairly expensive and nondisposable devices such as the endoscope. If it is intended to use the balloon only to dissect a tunnel, the balloon may be sealed to a disposable pushing member, and may be coupled to the pushing member with adhesives, heat sealing, or integral construction or any other coupling means. The balloon cover, sleeve or fairing 60 surrounds the balloon tube 49 and provides a protective sheath during placement of the balloon loaded dissector. The fairing may be a thin sheath of polyurethane or other plastic film, or it may be a more rigid or tube of PVC, PTFE, PETG, polyethylene, or other plastic. The balloon fairing 60 may be elastic or resilient so that it serves to compress the balloon 49, so that the balloon quickly and automatically collapses upon deflation. The fairing may be made resilient by choosing a resilient material, and a thin sheet of polyurethane is sufficiently resilient and elastic under the pressure used to inflate the balloon. The balloon itself may also be made of polyurethane, but made of a thick polyurethane which is nonelastomeric under the range of pressure used to inflate the balloon. Where the balloon and balloon cover are made of the same material or a miscible material or a material of comparable melting point, the balloon may be heat sealed to the balloon cover at various points to prevent the cover from inadvertently slipping off the balloon. Where the balloon and balloon cover are made of different, they may be attached with adhesive or other fastening means.

Figure 14:
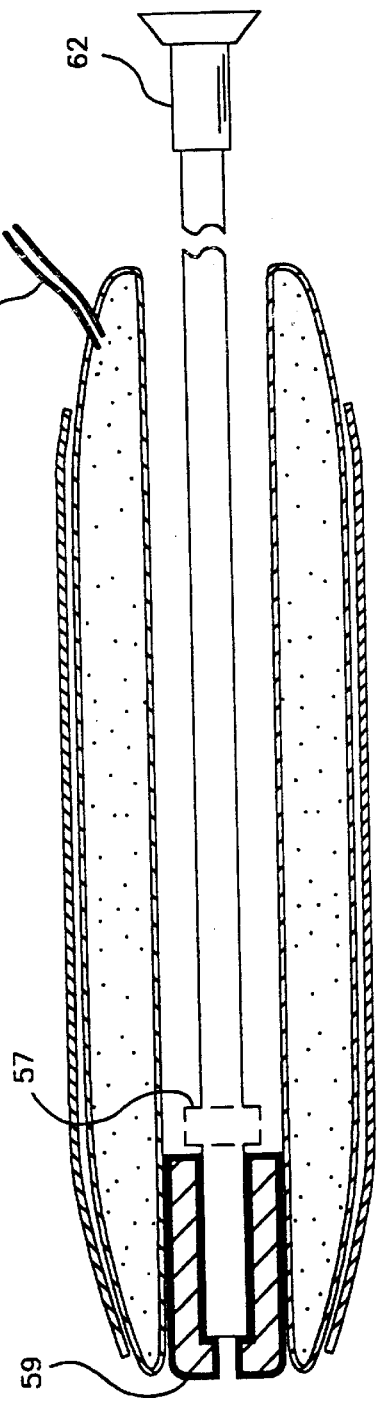
FIG. 14 shows the balloon dissector in its inflated state.

The balloon loaded blunt dissector is pushed along the blood vessel until the balloon tube is located over the desired length of the saphenous vein. When the balloon is properly in place it occupies a narrow tunnel over the saphenous vein. When in place, the balloon is inflated through inflation tube 61. As shown in FIG. 14, the outer walls expand under inflation and the fairing 60 stretches as the balloon membrane is inflated. The expansion of the balloon enlarges the tunnel. The outer diameter of the balloon tube defines the size of the tunnel which is created, and the outer diameter may be controlled during manufacture and during inflation. Also as shown in FIG. 14, the guide rod may be conveniently replaced with an endoscope 62 which can also serve as the pushing member. The endoscope can be chosen to have an outer diameter matching the support tube, or it can be provided with a stop collar, both constructions serving to couple the endoscope to the balloon tube so that pushing on the endoscope serves to push the balloon into the body.

When the balloon is deflated through the inflation tube, the fairing 60 serves to compress and collapse the balloon and squeeze the inflation fluid out of the balloon, thus returning the balloon to the diameter shown in FIG. 13. After the balloon has been collapsed by the elastic force of the fairing 60, the assembly may be further advanced or pulled back from its position in the body, and repositioned at another area of interest. When the balloon is repositioned, it may be reinflated to enlarge the tunnel. The balloon may be repeatedly inflated and deflated in this manner. Alternatively, the fairing 60 may be removed by pulling it proximally out of the incision to allow the balloon to enlarge.

Figure 15:
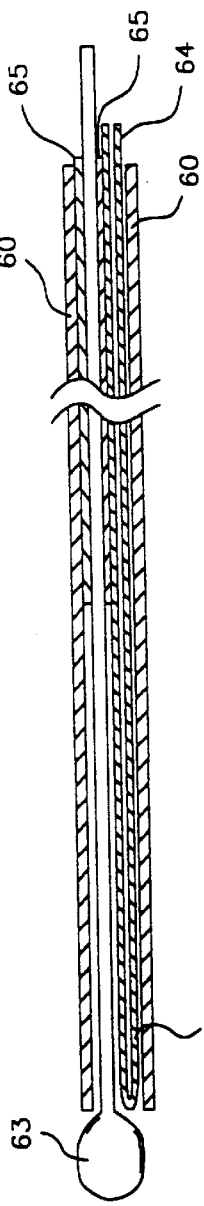
FIG. 15 shows a cross section of an alternate embodiment of the balloon loaded blunt dissector.

FIG. 16 shows an alternate embodiment of the balloon loaded blunt dissector. The guide rod is provided with a slender metal rod fitted with an enlarged tip or olive tip 63. The balloon 64 is a long slender cylindrical balloon, with, or without a central lumen. A monorail 65 is attached to the outside of the balloon and the guide rod fits through the guide rail. The balloon is uninflated in FIG. 15, and the balloon and guide rail are shown inside the fairing 60. The balloon of FIG. 15 is used in the same way as the balloon of FIGS. 13 and 14.

In operation, the balloon is slipped over the endoscope or guide rod and the balloon fairing is slipped over the balloon. The choice of endoscope is expected to be the preferred choice, because it allows visualization of the anatomy as the distal tip of the balloon pushes through the plane dividing the muscle and fascia. The assembly is inserted either directly into the incision or through a cannula. After the guide rod and balloon are in place near the perforating veins, the balloon cover can be pulled out of the incision, and may be provided with tear away perforations to facilitate removal. The balloon cover may be pulled back gradually, as the balloon is inserted, to uncover that portion of the balloon which is inside the body, and the balloon can be inflated to dissect a larger tunnel in the early stages of insertion. After full insertion, in a preferred method of use, the balloon may be left in place in the tunnel while the endoscope is inserted to view the interior surfaces of the body at the tip of the balloon, and endoscopic instruments are passed through the central lumen to ligate and divide the perforating veins encountered. In situations where it is desirable to insufflate the tunnel created by the balloon, the balloon may be deflated and pulled out of the tunnel through cutdown. 13, and a cannula port 16 with insufflation tube 17 may be inserted into the same cutdown as shown in FIG. 3b. A secondary endoscopic access port 19 may be inserted into the knee incision 12 to pass a variety of instruments into the workspace.

The devices and methods described above have been developed in the field of vascular surgery. However, it is readily apparent that the devices and methods may be used for dissecting long tunnels near other long organs of the body. Various arteries and veins must be dissected and mobilized for other operations, such as a coronary bypass operation, popliteal bypass, or a dialysis vein loop. In these operations, a vein must be harvested, and the sites at which the vein will be attached or amostosized must also be uncovered, and the devices and methods described above can be used in those operations. Other vessels may be dissected from surrounding tissue, such as fallopian tubes, spermatic cords, bile ducts, intestines, and others. These vessels may be dissected and mobilized laparoscopically using the techniques described above.

Where appropriate, the devices and methods may be used during open surgery to facilitate dissection of veins or arteries, in which case an initial working space is provided by the normal open surgery techniques. While the preferred embodiments of the devices and methods have been described, they are merely illustrative of the principles of the invention. Other embodiments and configurations may be devised without departing from the spirit of the inventions and the scope of the appended claims.

what is claimed is:

1. A method of treating a perforating vein in a human body, said perforating vein extending from a superficial location beneath the layer of skin and fat to a deep location within tissue underlying the skin and fat and fascia, said method comprising:

making a small incision through the skin;

inserting a dissector into the incision, the dissector comprising an elongate tubular member;

advancing the dissector under the skin, fat, and fascia to the vicinity of the perforating vein to be treated thereby creating a tunnel through the skin, fat, and fascia;

inserting a surgical instrument through said tubular member and advancing said surgical instrument to the location of the perforating vein;

performing a surgical procedure on the perforating vein with said surgical instrument.

2. The method of claim 1 wherein the elongate tubular member includes an endoscope installed in an endoscope channel formed therein, the method including the step of visualizing with the endoscope while advancing the dissector under the skin, fat, and fascia to the vicinity of the perforating vein.

3. The method of claim 1 wherein the dissector further comprises a balloon disposed on the distal end of the tubular member and further comprising:

inflating the balloon to expose the perforating vein from the surrounding tissue.

4. The method of claim 1 further comprising:

insufflating the tunnel created by the dissector.

5. The method of claim 4 further comprising:

removing the dissector prior to insufflating the tunnel.

6. The method of claim 2 further comprising the step of removing the endoscope from the tubular member prior to the step of inserting a surgical instrument through the tubular member.

7. The method of claim 3 further comprising:

deflating the balloon;

removing the dissector;

inserting an insufflation port;

insufflating the tunnel via the insufflation port.

8. The method of claim 2 wherein the dissector further comprises a everting balloon disposed on the distal end of the tubular member, the balloon everted and folded inside the tubular member prior to inflation, the method further comprising:

inflating the balloon to expose the perforating vein from the surrounding tissue.

9. The method of claim 8 further comprising:

insufflating the tunnel created by the dissector.

10. The method of claim 9 further comprising:

removing the dissector prior to insufflating the tunnel.

11. The method of claim 8 further comprising the step of removing the endoscope from the tubular member prior to the step of inserting a surgical instrument through the tubular member.

12. The method of claim 8 further comprising:

deflating the balloon;

removing the dissector;

inserting an insufflation port;

insufflating the tunnel via the insufflation port.

13. The method of claim 1 wherein the surgical procedure comprises dividing and ligating the perforating vein.

14. A method of treating a perforating vein in a human body, the perforating vein extending from a superficial location beneath the layer of skin and fat to a deep location within tissue underlying the skin and fat and fascia, the method comprising:

making a first small incision through the skin;

inserting a dissector into the incision, the dissector comprising an elongate tubular member having proximal and distal ends;

advancing the dissector under the skin, fat, and fascia to the vicinity of the perforating vein to be treated thereby creating a tunnel through the skin, fat, and fascia;

making a second small incision spaced apart from the incision, the second incision providing access to the perforating vein;

inserting an access port through the second incision;

inserting a surgical instrument through the access port and advancing the surgical instrument to the location of the perforating vein;

performing a surgical procedure on the perforating vein with the surgical instrument.

15. The method of claim 14 wherein the elongate tubular member includes an endoscope installed in an endoscope channel formed therein, the method including the step of visualizing with the endoscope while advancing the dissector under the skin, fat, and fascia to the vicinity of the perforating vein.

16. The method of claim 14 wherein the dissector further comprises a balloon disposed on the distal end of the tubular member and further comprising:

inflating the balloon to expose the perforating vein from the surrounding tissue.

17. The method of claim 14 further comprising:

insufflating the tunnel created by the dissector.

18. The method of claim 14 further comprising:

removing the dissector prior to insufflating the tunnel.

19. The method of claim 15 further comprising the step of removing the endoscope from the tubular member prior to the step of inserting a surgical instrument through the tubular member.

20. The method of claim 16 further comprising:

deflating the balloon;

removing the dissector;

inserting an insufflation port into the first incision; and insufflating the tunnel via the insufflation port.

* * * * *